(12) United States Patent
Utschig et al.

(10) Patent No.: US 7,687,790 B2
(45) Date of Patent: Mar. 30, 2010

(54) EMI SHIELDING OF DIGITAL X-RAY DETECTORS WITH NON-METALLIC ENCLOSURES

(75) Inventors: Michael John Utschig, Wauwatosa, WI (US); Habib Vafi, Brookfield, WI (US); William Andrew Hennessy, Schenectady, NY (US); Donald Earl Castleberry, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 325 days.

(21) Appl. No.: 11/759,829

(22) Filed: Jun. 7, 2007

(65) Prior Publication Data

US 2008/0304246 A1 Dec. 11, 2008

(51) Int. Cl.
*G02B 5/00* (2006.01)
*G21F 5/00* (2006.01)
*G21C 11/00* (2006.01)

(52) U.S. Cl. .............. 250/515.1; 250/505.1; 250/517.1

(58) Field of Classification Search ........................ None
See application file for complete search history.

(56) References Cited

U.S. PATENT DOCUMENTS

| | | | |
|---|---|---|---|
| 5,132,539 A | 7/1992 | Kwasnick | |
| 5,474,458 A | 12/1995 | Vafi | |
| 5,736,732 A | 4/1998 | Possin | |
| 6,073,343 A | 6/2000 | Petrick | |
| 6,438,210 B1 | 8/2002 | Castleberry | |
| 6,594,342 B2 | 7/2003 | Castleberry | |
| 6,642,524 B2 | 11/2003 | Vafi | |
| 6,720,561 B2 | 4/2004 | Baumgartner | |
| 6,784,434 B2 | 8/2004 | Hennessy | |
| 6,946,661 B2 | 9/2005 | Vafi | |
| 6,982,424 B2 | 1/2006 | Vafi | |
| 7,005,648 B2 | 2/2006 | Baumgartner | |
| 7,019,304 B2 | 3/2006 | Albagli | |
| 7,126,130 B2 | 10/2006 | Hennessy | |
| 2006/0065846 A1 | 3/2006 | Ertel | |
| 2007/0085015 A1 | 4/2007 | Castleberry | |
| 2007/0152388 A1 | 7/2007 | Utschig | |

FOREIGN PATENT DOCUMENTS

WO   WO9957952 A1 * 11/1999

* cited by examiner

*Primary Examiner*—David A Vanore
(74) *Attorney, Agent, or Firm*—Fletcher Yoder

(57) ABSTRACT

An imaging system is provided having an EMI shield configured to shield one or more imaging components. The EMI shield includes a first material having a first plurality of conductive elements integrally formed within a first nonconductive material and also includes a generally nonconductive exterior. A method is provided for shielding EMI in an imaging system. The method includes providing an EMI shielding enclosure that includes a first material having a first plurality of conductive elements disposed in a first non-conductive material, and a second material having a second plurality of conductive elements disposed in a second non-conductive material, wherein the first plurality of conductive elements engages the second plurality of conductive elements to form a conduction path. Another method for shielding EMI in an imaging system is provided, that includes providing an EMI shielding enclosure having a first material that has a non-conductive surface and a second EMI shielding material disposed on the non-conductive surface of the first material.

29 Claims, 6 Drawing Sheets

EMI SHIELDING OF DIGITAL X-RAY DETECTORS WITH NON-METALLIC ENCLOSURES

BACKGROUND

The invention relates generally to imaging devices and, more particularly, electromagnetic interference (EMI) shielding in portable digital x-ray detectors.

Portable imaging devices, such as portable x-ray detectors, often contain multiple electrical components, such as circuit boards, that may generate and/or be adversely affected by electromagnetic interference. Typically, the portable imaging devices have a metal housing (e.g., aluminum, magnesium, etc.) to provide the shielding required. For example, the housing or enclosure may be constructed from multiple pieces of magnesium. The metal housing provides a conductive shield around the sensitive electrical components of the imaging device, thereby containing EMI generated within the metal housing while also blocking external EMI from reaching the electrical components within the metal housing. Unfortunately gaps in the housing due to joints, seams, or turns can result in EMI and caring and/or escaping the metal housing. In addition, the metal housings are generally very heavy and add undesired weight to the portable imaging device.

BRIEF DESCRIPTION

Certain embodiments commensurate in scope with the originally claimed invention are set forth below. It should be understood that these embodiments are presented merely to provide the reader with a brief summary of certain forms the invention might take and that these embodiments are not intended to limit the scope of the invention. Indeed, the invention may encompass a variety of features that may not be set forth below.

In accordance with a first embodiment, an imaging system is provided. The imaging system includes an electromagnetic interference (EMI) shield configured to shield one or more imaging components from electromagnetic interference, wherein the EMI shield comprises a first material having a first plurality of conductive elements integrally formed within a first nonconductive material, wherein the first material has a first generally nonconductive exterior.

A method for shielding electromagnetic interference in an imaging system is provided. The method includes providing an electromagnetic interference (EMI) shielding enclosure comprising a first material consisting essentially of a first plurality of conductive elements disposed in a first non-conductive material and a second material consisting essentially of a second plurality of conductive elements disposed in a second non-conductive material, wherein the first plurality of conductive elements engages the second plurality of conductive elements to form a conduction path.

In accordance with a second embodiment, an imaging system is provided The imaging system includes image detection circuitry; and a portable enclosure disposed about the image detection circuitry and at least substantially made of first and second electromagnetic interference (EMI) shielding materials, wherein the first EMI shielding material comprises a first plurality of conductive elements disposed in a first non-conductive material and the second EMI shielding material comprises a second plurality of conductive elements disposed in a second non-conductive material, wherein the first and second plurality of conductive elements are conductively coupled together via a conduction path through non-conductive surfaces of the first and second EMI shielding materials.

In another embodiment, a method for shielding electromagnetic interference in an imaging system is provided. The method includes providing an EMI shielding enclosure comprising a first material having a non-conductive surface, wherein a second EMI shielding material is disposed on the non-conductive surface of the first material

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
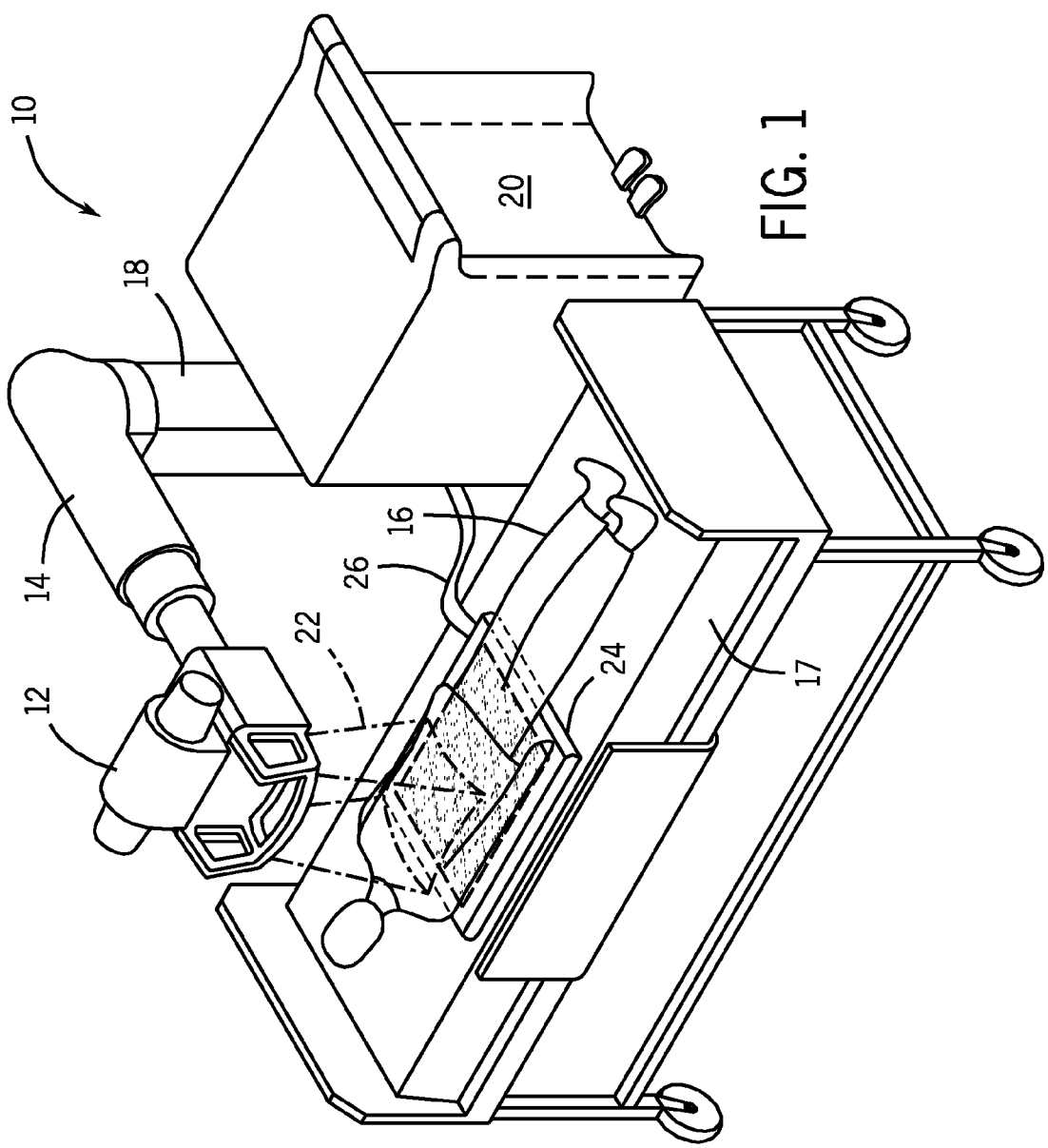
FIG. 1 is a perspective view of an embodiment of a mobile x-ray imaging system using a portable flat-panel digital x-ray detector.

In certain embodiments, as discussed below, internal electrical components of an imaging device are disposed within an EMI shielded external enclosure, wherein the electrical components are coupled to a support structure for grounding, support, and so forth. The external enclosure may provide continuous EMI shielding without an all-metal construction, thereby minimizing electrical noise and reducing the possibility of damage to the internal components while also minimizing the weight of the imaging device. In accordance with the embodiments described herein, the external enclosure comprises a material composition having a non-conductive matrix with conductive elements disposed in the non-conductive matrix. The material composition may be a compounded plastic, a composite material, or a combination thereof. As the outer portion or exterior layer of these material compositions is non-conductive, in order to create a continuous conductive path, minimize any gaps in the enclosure, and form a continuous EMI shield around the internal components, various novel techniques described herein provide for joining such materials at the joints, seams, and turns of the external enclosure. As discussed below, such techniques may include overmolded washers, overmolded studs, abraded surfaces, toothed metal fasteners, conductive tape and/or overmolding at the joints, turns and seams. Additionally, in some alternative embodiments, provide the material composition may be coated with a conductive layer to create sufficient EMI shielding characteristics. For example, the enclosure may include a secondary conductive layer such as a conductive paint sprayed on the surface, a metal plated onto the surface, or a metallic foil or woven fabric bonded to the surface, or a combination thereof.

The portable imaging device described herein may be used in a variety of imaging systems, such as medical imaging systems and non-medical imaging systems. For example, medical imaging systems include radiology (e.g., digital x-ray), mammography, tomosynthesis, and computed tomography (CT) imaging systems. These various imaging systems, and the different respective topologies, are used to create images or views of a patient for clinical diagnosis based on the attenuation of radiation (e.g., x-rays) passing through the patient. Alternatively, imaging systems may also be utilized in non-medical applications, such as in industrial quality control or in security screening of passenger luggage, packages, and/or cargo. In such applications, acquired data and/or generated images representing volumes or parts of volumes (e.g., slices) may be used to detect objects, shapes or irregularities which are otherwise hidden from visual inspection and which are of interest to the screener. In each of these imaging systems, the sensitive internal electrical components of the portable imaging device are disposed within an enclosure to physically protect the internal electrical components and shield from EMI.

Depending on the type of imaging device, the internal components may include a variety of circuits, panels, detectors, sensors, and other relatively delicate components. X-ray imaging systems, both medical and non-medical, utilize an x-ray tube to generate the x-rays used in the imaging process. The generated x-rays pass through the imaged object where they are absorbed or attenuated based on the internal structure and composition of the object, creating a matrix or profile of x-ray beams of different strengths. The attenuated x-rays impinge upon an x-ray detector designed to convert the incident x-ray energy into a form usable in image reconstruction. Thus, the x-ray profile of attenuated x-rays is sensed and recorded by the x-ray detector. X-ray detectors may be based on film-screen, computed radiography (CR) or digital radiography (DR) technologies. In film-screen detectors, the x-ray image is generated through the chemical development of the photosensitive film after x-ray exposure. In CR detectors, a storage phosphor imaging plate captures the radiographic image. The plate is then transferred to a laser image reader to "release" the latent image from the phosphor and create a digitized image. In DR detectors, a scintillating layer absorbs x-rays and subsequently generates light, which is then detected by a two-dimensional flat panel array of silicon photo-detectors. Absorption of light in the silicon photo-detectors creates electrical charge. A control system electronically reads out the electrical charge stored in the x-ray detector and uses it to generate a viewable digitized x-ray image.

In view of the various types of imaging systems and potential applications, the following discussion focuses on embodiments of a digital flat panel, solid-state, indirect detection, portable x-ray detector for use with a mobile x-ray imaging system. However, other embodiments are applicable with other types of medical and non-medical imaging devices, such as direct detection digital x-ray detectors. Additionally, other embodiments may be used with stationary or fixed room x-ray imaging systems. Further, the present application makes reference to an imaging "subject" and an imaging "object". These terms are not mutually exclusive and, as such, use of the terms is interchangeable and is not intended to limit the scope of the appended claims.

Turning now to FIG. 1, an exemplary mobile x-ray imaging system 10 employing a portable x-ray detector is illustrated. In the illustrated embodiment, the mobile x-ray imaging system 10 includes a radiation source 12, such as an x-ray source, mounted or otherwise secured to an end of horizontal arm 14. The arm 14 allows the x-ray source 12 to be variably positioned above a subject 16, resting on a patient table or bed 17, in such a manner so as to optimize irradiation of a particular area of interest. The x-ray source 12 may be mounted through a gimbal-type arrangement in column 18. In this regard, the x-ray source 12 may be rotated vertically from a rest or park position on the mobile x-ray unit base 20 to the appropriate position above the subject 16 to take an x-ray exposure of the subject 16. The rotational movement of column 18 may be limited to a value of 360 degrees or less to prevent entanglement of high voltage cables used to provide electrical power to the x-ray source 12. The cables may be connected to a utility line source or a battery in the base 20 to energize the x-ray source 12 and other electronic components of the system 10.

The x-ray source 12 projects a collimated cone beam of radiation 22 toward the subject 16 to be imaged. Accordingly, medical patients and luggage, packages, and other subjects or objects may be non-invasively inspected using the exemplary x-ray imaging system 10. A portable x-ray detector 24 placed beneath the subject 16 acquires the attenuated radiation and generates a detector output signal. The detector output signal may then be transmitted to the mobile imaging system 10 over a wired or a wireless link 26. The system 10 may be equipped with or connectable to a display unit for the display of images captured from the imaging subject 16.

Figure 2:
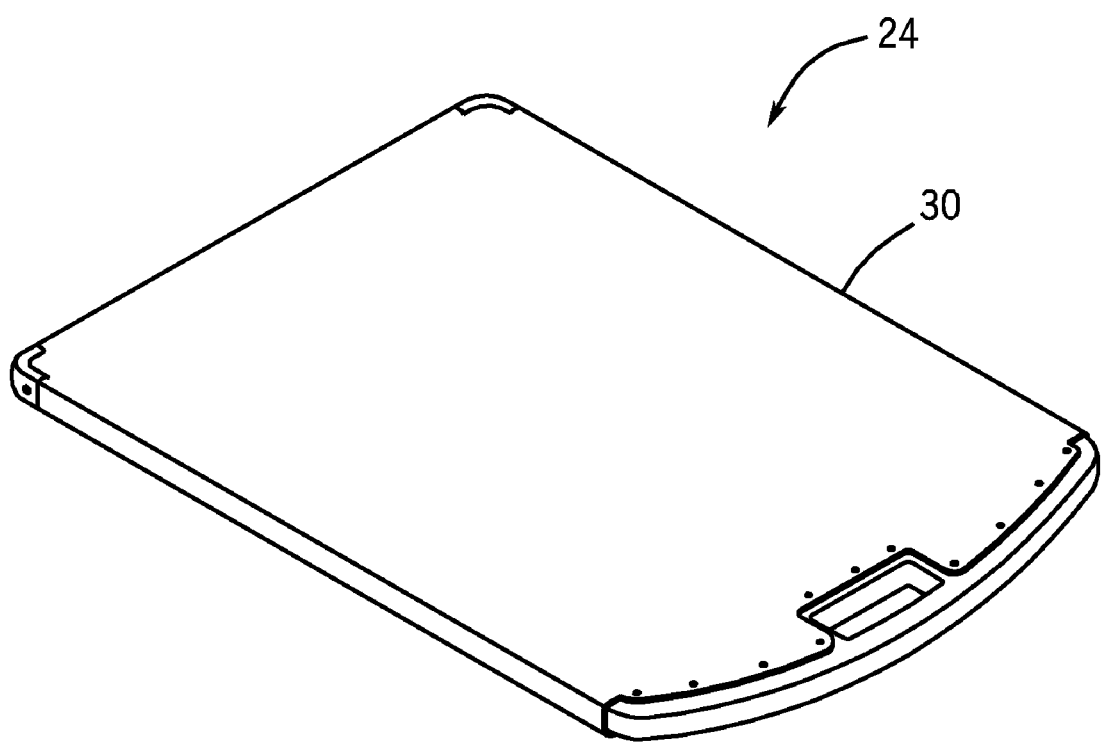
FIG. 2 is a perspective view of the portable flat panel digital x-ray detector of the imaging system of FIG. 1.

The exemplary imaging system 10, and other imaging systems based on radiation detection, employs the portable x-ray detector 24, such as a flat panel, digital x-ray detector. A perspective view of such an exemplary flat panel, digital x-ray detector 24 is provided in FIG. 2. However, as mentioned above, other embodiments of the detector 24 may include other imaging modalities in both medical and non-medical applications. The exemplary flat panel, digital x-ray detector 24 includes a detector subsystem for generating electrical signals in response to reception of incident x-rays.

In accordance with certain embodiments, a protective housing 30 provides an external enclosure to the detector subsystem, so as to protect the fragile detector components from damage when exposed to an external load or an impact. In addition, as discussed in further detail below, the housing 30 may be made of One or more material compositions having a non-conductive matrix with conductive elements disposed therein, and may provide EMI shielding to protect the internal components from external electronic noise. In general, the protective enclosure 30 may be a continuous structure and may be substantially devoid of any discontinuities. In some embodiments, the protective enclosure may be a 4-5 sided structure in a sleeve like configuration having at least one opening to allow for the insertion of the detector subsystem. It should be noted that the individual sides or edges of the single-piece sleeve may be flat, rounded, curved, contoured, or shaped to improve detector ruggedness and ease of use. In accordance with embodiments of the present invention, the protective enclosure 30 may be formed of a material composition such as a compounded plastic, a composite material, or a combination thereof. In some embodiments, the chosen material has low x-ray attenuation characteristics. Further, the chosen material may provide cost, weight, aesthetic, and ease of cleaning advantages over conventional materials. Additionally, the protective enclosure 30 may be designed to be substantially rigid with minimal deflection when subjected to an external load.

One or more corner or edge caps 32 may be provided at respective corners, edges, or a portion of respective edges of the protective enclosure 30. Further, a handle 34 may be mechanically coupled to the single-piece protective enclosure 30 to facilitate the portability of the detector 24. This handle may be a separate component, which is attached to the single-piece protective enclosure 30. As will be described in detail below, the corners or end caps 32, the handle 34, and/or any other area of the enclosure 30 may be formed of a compounded plastic, a composite material, or a combination thereof. Alternatively, in certain embodiments, the handle 34 may be a continuous extension of the protective enclosure 30. In other words, the handle 34 may be formed integrally with the single-piece protective enclosure, thereby eliminating or minimizing the mechanical attachment points between the handle 34 and the protective enclosure 30. A removable edge cap may be provided in such embodiments to allow for the insertion of the detector subsystem into the single-piece protective enclosure 30.

As shown, the detector 24 may be constructed without a fixed tether. Alternatively, the detector may be connected to a tether that is used to connect the detector readout electronics to the data acquisition system of the scanner when in use. When not in use, the detector may be easily detached from tether and stored remotely from the imaging system. As such, the detector 24 may be transported to and from multiple scan stations remote from one another. This is particularly advantageous for emergency rooms and other facilities. The portability and detachability of the detector further enhances the mobility of a mobile x-ray imaging system, such as that shown in FIG. 1.

Figure 3:
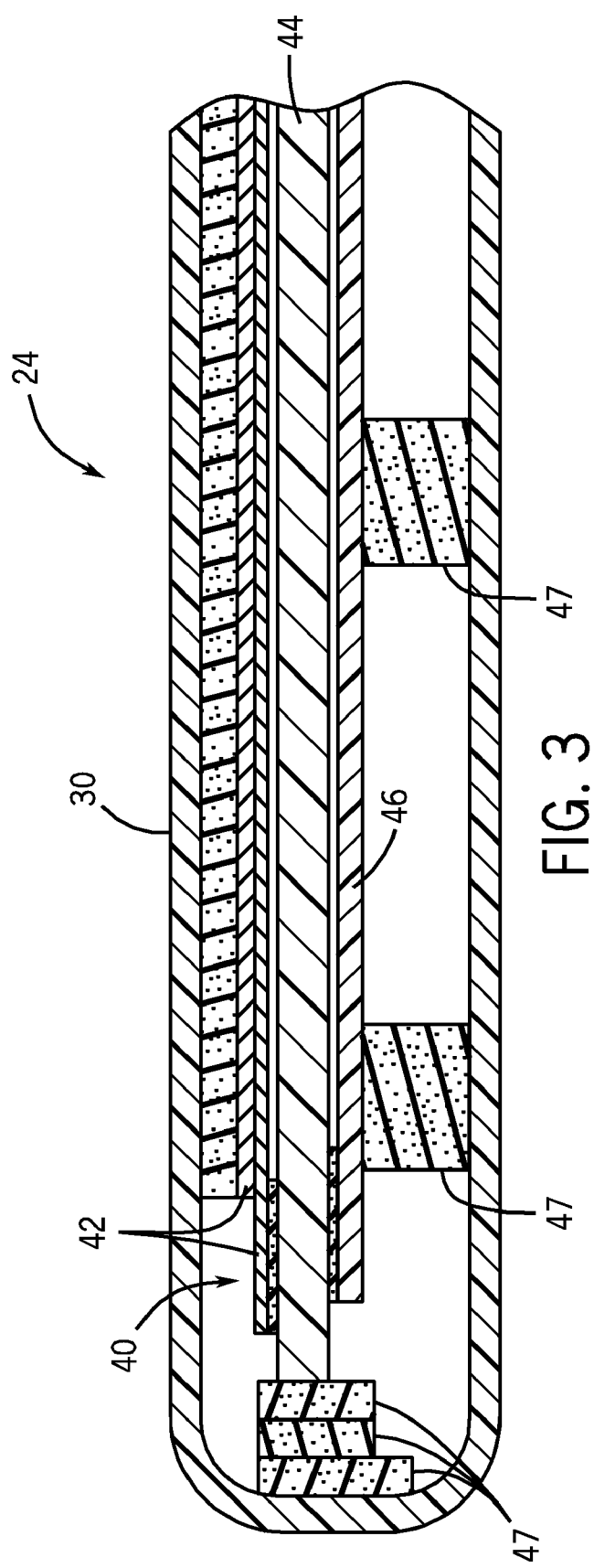
FIG. 3 is a cross-sectional view of an embodiment of the portable flat panel digital x-ray detector illustrated in FIG. 2.

Referring now to FIG. 3, a cross-sectional view of an embodiment of the portable flat panel digital x-ray detector 24 is shown. Again, as mentioned above, the internal components (e.g., subsystem 40) may include a variety of imaging components, such as radiography (e.g., digital x-ray), computed tomography, mammography, and so forth. The illustrated detector subsystem 40 includes an imaging panel 42, an electronics support structure 44, and associated electronics 46. Additional internal supports 47 may be provided to physically support the detector subsystem 40 inside the enclosure 30.

The imaging panel 42 includes a scintillator layer for converting incident x-rays to visible light. The scintillator layer, which may be fabricated from Cesium Iodide (CsI) or other scintillating materials, is designed to emit light proportional to the energy and the amount of the x-rays absorbed. As such, light emissions will be higher in those regions of the scintillator layer where either more x-rays were received or the energy level of the received x-rays was higher. Since the composition of the subject will attenuate the x-rays projected by the x-ray source to varying degrees, the energy level and the amount of the x-rays impinging upon the scintillator layer will not be uniform across the scintillator layer. This variation in light emission will be used to generate contrast in the reconstructed image.

The light emitted by the scintillator layer is detected by a photosensitive layer on the 2D flat panel substrate. The photosensitive layer includes an array of photosensitive elements or detector elements to store an electrical charge in proportion to the quantity of incident light absorbed by the respective detector elements. Generally, each detector element has a light sensitive region and a region including electronics to control the storage and output of electrical charge from that detector element. The light sensitive region may be composed of a photodiode, which absorbs light and subsequently creates and stores electronic charge. After exposure, the electrical charge in each detector element is read out using logic-controlled electronics 46.

The various components of detector subsystem 40 may be protected or secured against the enclosure 30 by one or more internal supports 47 disposed about all sides of the internal components within the external protective enclosure 30. In certain embodiments, the detector subsystem 40 may be described as free-floating within the external protective enclosure 30 via the internal supports 47. For example, the internal supports 47 may be formed of a resilient material or spring assembly, such that the detector subsystem 40 is not rigidly fixed in a position relative to the external protective enclosure 30. In other words, the detector subsystem 40 may have at least some freedom to move in all directions within the enclosure 30 via a resilient or spring-like embodiment of the supports 47. The internal supports 47 may be a shock absorbent material, and the freedom of movement may be varied depending on the degree of compressibility of the shock absorbent material. In some embodiments, the internal supports 47 may be formed from a rubber, a foam, an elastomer, a foam rubber, another elastic material, or a combination thereof. The supports 47 are also generally lightweight, and may include single-sided or double-sided adhesive surfaces to facilitate the attachment to the external protective enclosure 30 and/or the detector subsystem 40. In other embodiments, the supports 47 may include a conductive pathway (or may be formed of a conductive material) to facilitate electrical and thermal conduction between the internal components, e.g., 42, 44, and 46, and the enclosure 30.

In certain embodiments, the supports 47 may be disposed between the detector subsystem 40 and the inner surface of the single-piece protective enclosure 30 to hold the detector subsystem 40. For example, one or more layers, strips, blocks, sheets, or panels 47 may be disposed on all six sides (e.g., top, bottom, left, right, front, and rear) of the detector subsystem 40 within the protective enclosure 30. In certain embodiments, the supports 47 may include multiple layers of different materials, different geometries (e.g., rectangular, circular, triangular, etc.), different dimensions (e.g., length, width, thickness, etc.), or combinations thereof. These structures are generally in contact with both the detector subsystem 40 and the protective enclosure 30 without any gap. In this manner, supports 47 act both as positional supports and shock absorbers for the detector subsystem 40. Again, the detector subsystem 40 may be described as suspended or free floating within the single-piece protective enclosure 30 via the supports 47, rather than being rigidly attached to the external protective enclosure 30. However, in other embodiments, the supports 47 may be formed of a resilient or non-resilient conductive material, such as metal, a compounded plastic, a composite, or a combination thereof.

The imaging panel 42 and associated electronics 46 are supported by a thin and lightweight electronics support structure 44. The readout electronics and other electronics 46 are disposed on the electronics support structure 44 on the side opposite from the imaging panel 42. That is, the electronics support structure 44 mechanically isolates the imaging components of the imaging panel 42 from the readout electronics 46.

In certain embodiments in accordance with the present invention, the housing 30 is substantially formed of a material composition having a non-conductive matrix material and conductive elements disposed in the non-conductive matrix material. The material composition may be a compounded plastic, a composite material, or a combination thereof. In one embodiment, the housing 30 may be substantially formed of a compounded plastic having a base resin of polycarbonate and additives of stainless steel fibers, carbon powder, carbon fibers, or a combination thereof. In other embodiments, the housing 30 may be substantially formed of composite materials having an epoxy matrix and graphite, carbon fibers, or a combination thereof. The housing 30 provides a lightweight yet stiff assembly to also protect and provide electronic shielding (e.g., EMI shielding) of imaging panel 42 and associated electronics 46. The construction of housing 30 from non-metallic materials (as opposed to conventional construction entirely with metal or metal alloys) in combination with other optimized materials used in construction of additional components or structures of the x-ray detector 24 reduces weight and cost while providing mechanical stiffness, energy absorption capability, ruggedness, and easier cleaning.

The compounded plastics used to construct the enclosure 30 may include a base resin and additives or fillers. The base resin may be a thermoset or thermoplastic, such as polycarbonate. The compounded plastic may be injection molded to form the thin and lightweight enclosure 30. In certain embodiments the surface of the injection molded enclosure 30 is primarily resin material and therefore is highly non-conductive. The additives may be stainless steel fibers, carbon powder, carbon fibers, or any conductive additive or filler that may be added to the base resin to provide conductive capabilities while maintaining the advantageous physical properties of the non-conductive plastic resin.

The composite materials used to construct the enclosure 30 may be combinations of a matrix having a reinforcement material. The matrix material, such as an epoxy, surrounds and supports the reinforcement material. The reinforcement materials, such as organic or inorganic fibers or particles, are bound together by the matrix of the composite. For fiber reinforcements, the direction the individual fibers may be oriented to control the rigidity and the strength of the composite. Further, the composite may be formed of several individual layers with the orientation or alignment of the reinforcement layers varying through the thickness of composite. The layers of the composite could use multiple materials in different forms (particles, fibers, fabric, thin foils, etc.). In one embodiment, the composite material for the enclosure 30 may be an epoxy matrix with layers of carbon fibers. However, any non-conductive matrix and conductive fibers may be used.

As discussed above, the imaging panel 42 and the associated electronics 46 are susceptible to interference from external electronic devices, and such external devices may also be affected by the electronic noise generated by the imaging panel 42 and associated electronics 46. Further, regulatory agencies such as the Federal Communications Commission (FCC) may restrict the amount of EMI emitted by some devices. In certain embodiments, the housing or enclosure 30 provides the desired EMI shielding for the internal components. However, without tapping into the conductive material, the non-metallic material compositions used to construct the lightweight housing 30 may generally have relatively poor conductivity compared to the conventional metallic materials used to form the housing 30, such as metals and metal alloys. Thus, the disclosed embodiments tap into and connect the conductive materials in the one or more parts of the housing 30. Further, it is desirable to make the EMI shield continuous around the entire x-ray subsystem 40. Any non-conductive gaps, spaces, and/or breaks in the EMI shield may reduce the effectiveness of the housing 30 as an EMI shield. Such non-conductive gaps, spaces, or breaks may be problematic especially in the case of multiple non-metallic material compositions used to form the housing 30. As described in detail below with reference to FIGS. 4-7, entrance paths may be created in the non-metallic material compositions at the joints, turns, and seams of the housing 30 to provide for a continuous conductive path, and therefore a continuous EMI shield, through the conductive cores or fibers of such materials. Otherwise, the presence of conduction paths at the joints, turns, and seams minimizes EMI that could affect operation of the imaging panel 42 and/or associated electronics 46. Thus, the entrance paths make the non—metallic material compositions and effective via my shields by interconnecting and generally using the conductive materials that are otherwise contained within the non-conductive matrix.

Figure 4A:
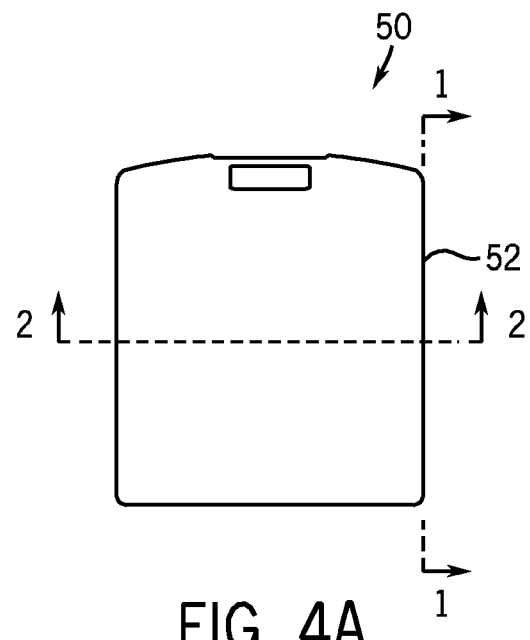
FIG. 4A is a top view of a compounded plastic housing used in accordance with an embodiment of the present technique.
Figure 4B:
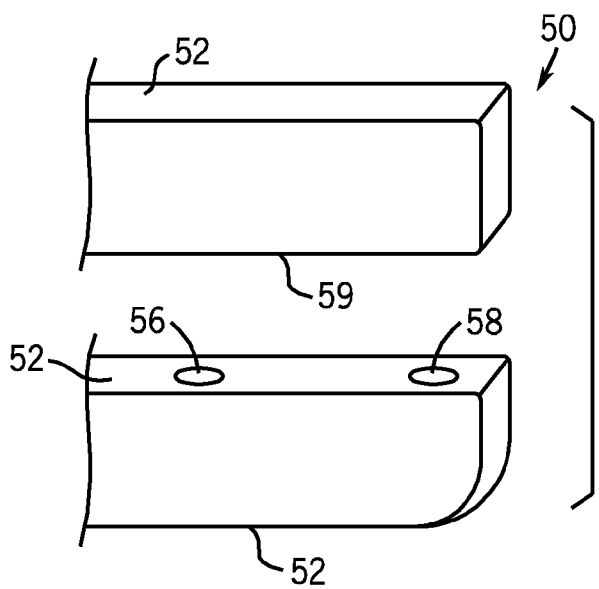
FIG. 4B is a cross-sectional view along line 1-1 of FIG. 4A illustrating a compounded plastic housing with overmolded washers in accordance with an embodiment of the present technique.
Figure 4C:
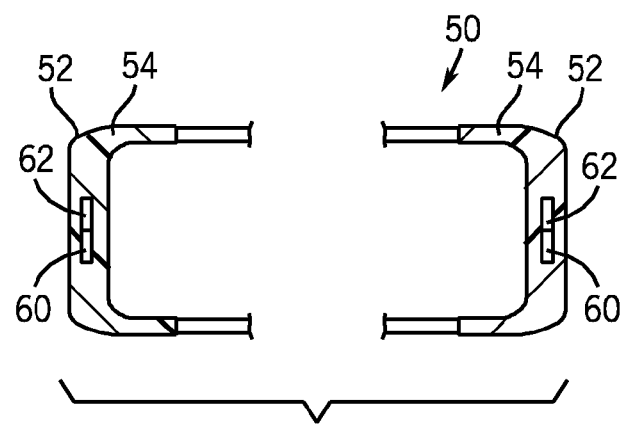
FIG. 4C is a cross-sectional view along line 2-2 of FIG. 4A illustrating a compounded plastic housing with overmolded metal studs in accordance with an embodiment of the present technique.

Turning now to FIG. 4A, a top view of a housing 50 formed from a compounded plastic is shown. The housing 50 has a non-conductive outer surface 52, such as polycarbonate, and a conductive core 54, such as carbon fibers. As discussed above, the non-conductive surface 52 of the compounded plastic may be any non-conductive plastic resin or polymer, and the conductive core 54 material may be additives specifically included to increase the conductive properties of the core of the plastic, such as carbon fibers, carbon powder, stainless steel fibers, or a combination of any of these materials. The conductive core 54 provides EMI shielding across the majority of the housing 50. The remainder of the EMI shielding may be maintained at the seams, joints, and turns through various techniques such as abrading or roughening the surface of the compounded plastic to expose the conductive elements and applying EM-gaskets to the exposed areas, overmolding a conductive interface structure and applying conductive tape or other conductive material, extending the parts over one another, or a combination thereof. For example, FIG. 4B depicts a cross section of the compounded plastic housing 50 of FIG. 4A taken along line 1-1, illustrating an overlap or seam in the housing 50 of FIG. 4A. The seam depicted in 4B maintains good EMI shielding through a conductive path formed by overmolding conductive interface structures, such as washers 56 and 58 in the compounded plastic. The overmolded washers 56 and 58 make contact with the conductive core of the compounded plastic, and then may contact a conductive surface on the other side 59 of the overlap or seam. For example, the other side of the seam or overlap may have conductive interface structures or an abraded surface to provide a conductive mating surface for the washers. Additionally, a conductive tape or other conductive material may be applied across the washers or an abraded surface. For example, FIG. 4C depicts a cross section of the compounded plastic housing 50 of FIG. 4A taken along line 2-2. As can be seen in the figure, the compounded plastic is joined at the seams 60, and the conductive cores 54 are in contact and from a conductive path. Further, conductive tape 62 is applied across the seams to complete the EMI shielding across the seam.

Figure 5A:
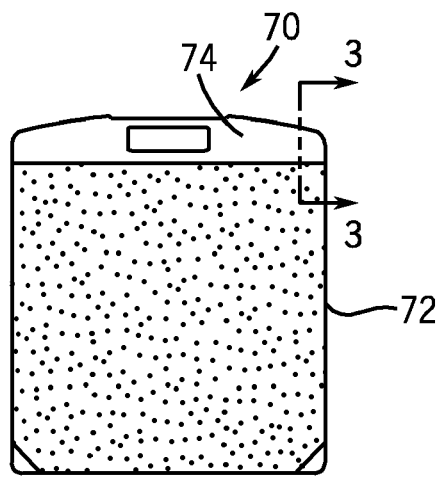
FIG. 5A is a top view of a compounded plastic and composite housing used in accordance with an embodiment of the present technique.
Figure 5B:
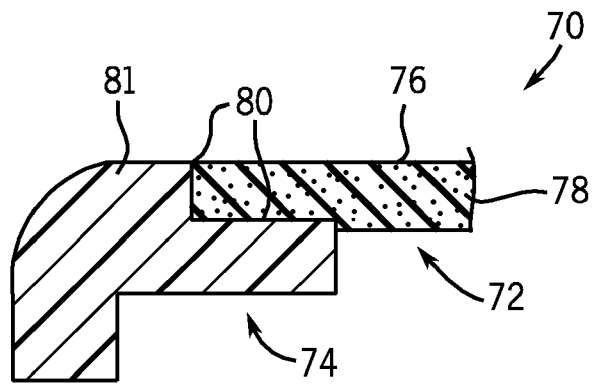
FIG. 5B is a cross-sectional view along line 3-3 of FIG. 5A illustrating an abraded surface between the compounded plastic and composite material of the housing in accordance with an embodiment of the present technique.
Figure 5C:
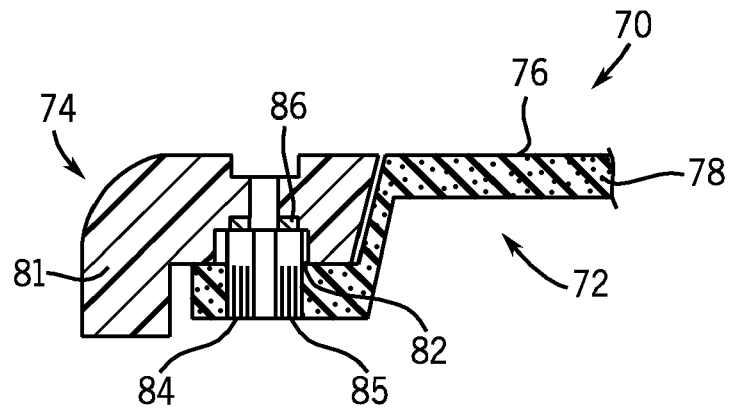
FIG. 5C is a cross-sectional view along line 3-3 of FIG. 5A illustrating an overmolded stud and toothed fastener between the compounded plastic and composite material of the housing in accordance with an embodiment of the present technique.

Referring now to FIG. 5A, a housing 70 formed primarily from composite materials 72 with the handle, corners, and other areas being formed from a compounded plastic 74. The composite material 72 has a non-conductive matrix 76, such as an epoxy matrix, and a conductive material 78 such as carbon fibers, disposed in the non-conductive matrix 76. As discussed above, the non-conductive matrix 72 of the composite material may be any non-conductive resin or epoxy, and the conductive material 78 may be fibers or other material specifically included to increase the EMI shielding properties. Conductivity, and thus EMI shielding, may be maintained between the composite material 72 and the compounded plastic 74 at the seams, joints, and turns through various techniques, such as overlapping the adjacent parts on the lengths and right turns, abrading the surface of the composite and/or compounded plastic to expose the conductive materials and create a conductive path; inserting a toothed metal fastener into a hole in the composite; and/or applying conductive tape across the joint. For example, FIG. 5B depicts a cross section of the housing 70 taken along line 3-3, showing a joint 80 between the composite material 72 and the compounded plastic 74. The surface of the composite material 72 is abraded to expose the conductive material 78; similarly, the compounded plastic 74 also has an abraded surface to expose the conductive additives 81. In addition to the conductive path formed by mating the exposed conductive surfaces together, a conductive tape or other conductive material may be applied at the joint to further maintain EMI shielding.

In an alternative embodiment depicted in the cross section of FIG. 5C, again taken along 3-3, the EMI shielding is maintained across a joint 82 through the insertion of a toothed metal fastener 84 in the composite material 72. The metal fastener 84 is driven into a hole in the composite material 72, and the teeth 85 of the metal fastener 84 contact the conductive fibers 76 and form a conductive entrance path. To complete the EMI shielding across the joint, the metal fastener 84 may make contact with an overmolded conductive interface structure in the compounded plastic, such as a washer 86. As will be appreciated, however, the composite material 72 may be joined to the compounded plastic 74 at a joint, seam, or turn through any one or a combination of the techniques and embodiments described above.

Figure 6A:
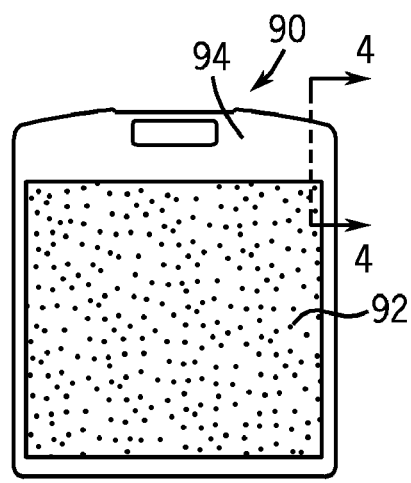
FIG. 6A is a top view of a compounded plastic and composite housing used in accordance with an embodiment of the present technique.
Figure 6B:
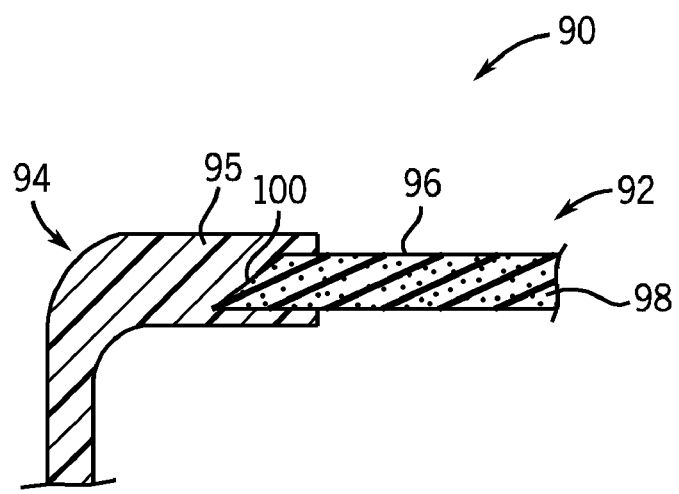
FIG. 6B is a cross-sectional view along line 4-4 of FIG. 6A illustrating an angled abraded surface of the composite and an abraded surface of the compounded plastic of the housing in accordance with an embodiment of the present technique.

Turning now to FIG. 6A, a top view of a housing 90 is shown that is formed nearly equally of a composite material 92 and a compounded plastic 94. The back, sides, corners, and handle of the housing 90 are formed from the compounded plastic 94 and the imaging area is formed from the composite material 92. As discussed above, the composite material 92 has a non-conductive matrix 96, such as an epoxy matrix, and a conductive material 98, such as carbon fibers, disposed in the non-conductive matrix 96. The non-conductive matrix 96 of the composite material 92 may be any non-conductive resin or epoxy, and the conductive material 96 may be fibers or other material specifically included to increase the conductive properties. In the embodiment depicted in FIGS. 6A and 6B, the EMI shield is maintained at the joint between the composite material 92 and the compounded plastic 94 by abrading the surface of the composite material 92 and overmolding the compounded plastic 94. For example, FIG. 6B depicts a cross section of the housing 90 taken along line 4-4, showing the composite material 92 with an abraded and angled edge 100. Abrading the composite edge exposes the conductive fibers 92 and creates an entrance path into the fiber core 98 of the composite material 92. The compounded plastic 94 is overmolded around the composite material 92 such that the conductive additives 95 of the compounded plastic 94 become intimate with the exposed core 98 of the composite material 92, forming a continuous conductive path and thus an EMI shield across the joint and throughout the enclosure 90. For any areas that are formed primarily from the compounded plastic 94, such as the back of the housing 90, EMI shielding may be maintained according to the techniques described in FIGS. 4A-4C.

Figure 7:
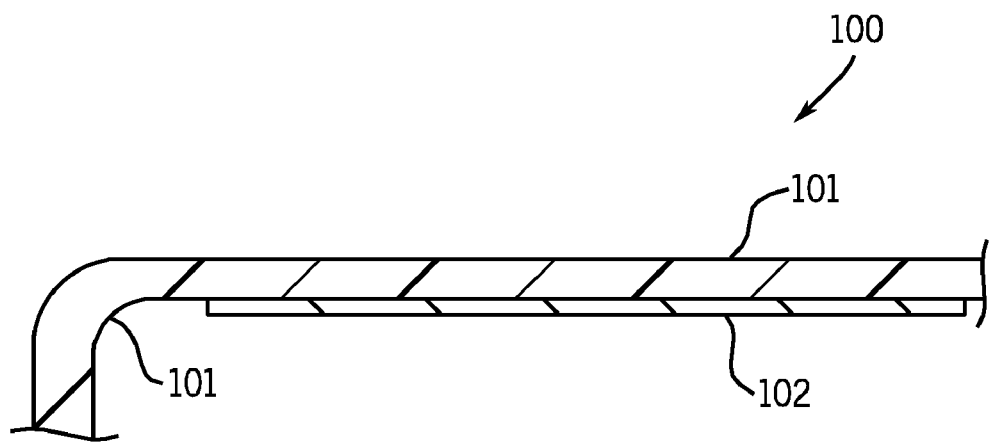
FIG. 7 is a cross-sectional view of a compounded plastic housing with a secondary conductive layer in accordance with an embodiment of the present technique.

Turning now to FIG. 7, a cross-section of a non-metallic housing 100 with a non-conductive surface 101 of a portable x-ray detector is depicted. The non-non-metallic housing 100 has a conductive second layer 102 disposed on the non-conductive surface 101 in accordance with an embodiment of the present technique. The non-metallic housing 102 may be the composite materials or compounded plastics described herein, or any other material with a non-conductive surface. The secondary conductive layer 102 may be any conductive layer that can be applied to the non-metallic housing 100 and enhance or create EMI shielding capability. In one embodiment, the secondary layer 102 may be a conductive paint sprayed onto the surface 101 and then cured. The conductive paint may contain copper, silver or any metal particles to increase conductivity and create EMI shielding properties on the surface 101. In a second embodiment, the secondary layer 102 may be a metal, such as copper and/or nickel, and may be deposited on the surface 101. The metal may be deposited though electroplating, or may be deposited through a chemical reduction process such as electro-less plating. In a third embodiment, the secondary layer may be a metallic foil or woven fabric having conductive properties. For example, the woven fabric may be coated with copper and/or nickel. The foils or fabrics may be bonded to the surface 101 of the non-metallic housing 102 through use of an adhesive, such as a pressure sensitive adhesive or other type of wet adhesive. Further, the foils or fabrics may be pre-bonded to a carrier layer and then overmolded to non-metallic parts in the non-metallic housing 100.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging system, comprising:
   an electromagnetic interference (EMI) shield configured to shield one or more imaging components from electromagnetic interference, wherein the EMI shield comprises a first material having a first plurality of conductive elements integrally formed within a first nonconductive material, wherein the first material has a first generally nonconductive exterior; and
   a conductive member having first and second portions, wherein the first portion extends into a first recess into the first material through the first generally nonconductive exterior in contact with the first plurality of conductive elements, and the second portion protrudes outside of the first generally nonconductive exterior.

2. The imaging system of claim 1, wherein the EMI shield surrounds an image detector panel.

3. The imaging system of claim 1, wherein the EMI shield at least substantially defines a panel-shaped portable housing.

4. The imaging system of claim 1, comprising an imaging component shielded by the EMI shield.

5. The imaging system of claim 4, wherein the imaging component comprises an x-ray component.

6. The imaging system of claim 1, wherein first plurality of conductive elements comprise fibers, particles, or a combination thereof.

7. The imaging system of claim 1, wherein the first material comprises a composite material, a compounded plastic, or a combination thereof.

8. The imaging system of claim 1, wherein the first plurality of conductive elements comprises stainless steel fibers and the first nonconductive material comprises polycarbonate.

9. The imaging system of claim 1, wherein the first plurality of conductive elements comprises carbon particles, or fibers, or a combination thereof, and the first nonconductive material comprises polycarbonate.

10. The imaging system of claim 1, wherein the EMI shield comprises a first component made of the first material and a second component made of a second material different from the first material, wherein the second material comprises a second plurality of conductive elements integrally formed within a second nonconductive material, and the second material has a second generally nonconductive exterior, wherein the second portion of the conductive member extends into a second recess into the second material through the second generally nonconductive exterior in contact with the second plurality of conductive elements.

11. The imaging system of claim 1, comprising a secondary shielding layer.

12. The imaging system of claim 11, wherein the secondary shielding layer comprises a conductive paint, a metallic foil, a woven fabric, or a combination thereof.

13. A method for shielding electromagnetic interference in an imaging system, comprising:
providing an electromagnetic interference (EMI) shielding enclosure comprising a first material consisting essentially of a first plurality of conductive elements disposed in a first non-conductive material and a second material consisting essentially of a second plurality of conductive elements disposed in a second non-conductive material; and
conductively coupling the first material with the second material to form a conduction path between the first plurality of conductive elements and the second plurality of conductive, wherein conductively coupling comprises abrading a non-conductive surface of the first material, or the second material, or both, to reveal a conductive surface having at least some of the conductive elements exposed.

14. The method of claim 13, wherein conductively coupling the first material with the second material comprises extending a conductive interface structure into a recess in the first material or the second material.

15. The method of claim 14, wherein extending the conductive interface structure comprises inserting or overmolding a metal stud in the first material or the second material.

16. The method of claim 13, wherein the first material, or the second material, or both comprise a compounded plastic.

17. The method of claim 13, wherein the first material, or the second material, or both comprise a composite material.

18. An imaging system, comprising:
image detection circuitry; and
a portable enclosure disposed about the image detection circuitry, wherein the portable enclosure comprises;
a first component at least substantially made of a first electromagnetic interference (EMI) shielding material, wherein the first EMI shielding material comprises a first plurality of conductive elements disposed in a first non-conductive material, and the first component comprises a first non-conductive surface disposed over the first EMI shielding material;
a second component at least substantially made of a second electromagnetic interference (EMI) shielding material, wherein the second EMI shielding material comprises a second plurality of conductive elements disposed in a second non-conductive material, the second component comprises a second non-conductive surface disposed over the second EMI shielding material, the first and second components are coupled together along an interface, and the first and second plurality of conductive elements are conductively coupled together via a conduction path through the first and second non-conductive surfaces along the interface.

19. The system of claim 18, wherein the conductive path comprises a conductive stud overmolded in the first EMI shielding material, or second EMI shielding material, or both.

20. The system of claim 18, wherein the conductive path comprises an abraded surface of the first EMI shielding material, or second EMI shielding material, or both.

21. The system of claim 18, wherein the image detection circuitry comprises an x-ray detector panel.

22. The system of claim 18, wherein the portable enclosure has a panel-shaped geometry.

23. The system of claim 18, wherein the first non-conductive material, or the second non-conductive material, or both, comprises polycarbonate, and the first plurality of conductive elements, or the second plurality of conductive elements, or both, comprises carbon fibers, or carbon powder, or stainless steel fibers, or a combination thereof.

24. The system of claim 18, wherein the first EMI shielding material or the second EMI shielding material is a compounded plastic.

25. The system of claim 18, wherein the first EMI shielding material or the second EMI shielding material is a composite material.

26. A method for shielding electromagnetic interference (EMI) in an imaging system, comprising:
providing an EMI shielding enclosure comprising a first material having a non-conductive surface, wherein a second EMI shielding material is disposed on the non-conductive surface of the first material; and
electroplating or electroless plating the EMI shielding material onto the non-conductive surface of the first material.

27. The method of claim 26, comprising painting the second EMI shielding material onto the non-conductive surface of the first material.

28. The method of claim 26, wherein the second material comprises a metallic foil.

29. The method of claim 26, wherein the second material comprises a woven fabric.

* * * * *